US010526563B2

(12) United States Patent
Schatkowski et al.

(10) Patent No.: US 10,526,563 B2
(45) Date of Patent: Jan. 7, 2020

(54) MIXTURES HAVING (4AR,5R,7AS, 9R)-OCTAHYDRO-2,2,5,8,8,9A-HEXAMETHYL-4H-4A, 9-METHANOAZULENO(5,6-D)-1,3-DIOXOLE) (AMBROCENIDE®)

(71) Applicant: SYMRISE AG, Holzminden (DE)

(72) Inventors: Dietmar Schatkowski, Einbeck (DE); Daniela Knoop, Holzminden (DE); Stefan Lambrecht, Hehlen (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/312,545

(22) PCT Filed: Feb. 26, 2015

(86) PCT No.: PCT/EP2015/054027
§ 371 (c)(1),
(2) Date: Nov. 18, 2016

(87) PCT Pub. No.: WO2015/176833
PCT Pub. Date: Nov. 26, 2015

(65) Prior Publication Data
US 2017/0114299 A1 Apr. 27, 2017

(30) Foreign Application Priority Data
May 21, 2014 (EP) .................... 14169354

(51) Int. Cl.
*C11B 9/00* (2006.01)
*C07D 317/70* (2006.01)

(52) U.S. Cl.
CPC .......... *C11B 9/0076* (2013.01); *C07D 317/70* (2013.01)

(58) Field of Classification Search
CPC ................................................. C11B 9/0076
See application file for complete search history.

(56) References Cited

U.S. PATENT DOCUMENTS 5,892,062 A * 4/1999 Pickenhagen ......... C11B 9/0076
512/12

FOREIGN PATENT DOCUMENTS

| CN | 1244527 A | 2/2002 |
| EP | 0 857 723 A1 | 8/1998 |
| EP | 1 634 864 A2 | 3/2006 |
| EP | 1 634 864 A3 | 8/2006 |

OTHER PUBLICATIONS

Panten, et al. ("New Woody and Ambery Notes from Cedarwood and Turpentine Oil", Chemistry and Biodiversity, vol. 1 (2004), p. 1936-1948). (Year: 2004).*
Panten J et al., "New Woody and Ambery Notes from Cedarwood and Turpentine Oil," Chemistry & Biodiversity, vol. 1, No. 12, (2004), pp. 1936-1948, XP-002543298.
International search report and written opinion under Rule 43 PCT attached to the search report, PCT/EP2015/054027.
Chinese Office Action dated Jul. 6, 2018 corresponding to Chinese Application No. 201580026098.0 and English translation thereof.
Tang, Jian et al., "Synthesis of Cedranone," Liaoning Chemical Industry, vol. 38, No. 7, 2009, pp. 453, 454 and 463.

* cited by examiner

*Primary Examiner* — Arrie L Reuther
(74) *Attorney, Agent, or Firm* — Polsinelli PC

(57) ABSTRACT

The present invention relates in particular to a mixture comprising or at least essentially consisting of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib), wherein the weight ratio of the compound of the formula (Ia) to the compound of the formula (Ib) in the mixture is in the range from 90:10 to 99:1. The present invention further relates to a method for producing such a mixture, to new odorant and/or aroma substance compositions, and to the use of a mixture of the invention (a) for masking or diminishing the one or more unpleasant olfactory impressions of one or more unpleasantly smelling substances, and/or (b) for intensifying the one or more pleasant olfactory impressions of one or more pleasantly smelling substances.

17 Claims, No Drawings

MIXTURES HAVING (4AR,5R,7AS,9R)-OCTAHYDRO-2,2,5,8,8,9A-HEXAMETHYL-4H-4A,9-METHANOAZULENO(5,6-D)-1,3-DIOXOLE)(AMBROCENIDE®)

CROSS-REFERENCE TO RELATED APPLICATIONS

This application is a national stage application (under 35 U.S.C. § 371) of 085158-556768, filed Feb. 26, 2015, which claims benefit of European Application No. 14169354.9, filed May 21, 2014, which are incorporated herein by reference in their entireties.

DISCLOSURE

The present invention relates to a mixture comprising or at least essentially consisting of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib), wherein the weight ratio of the compound of the formula (Ia) to the compound of the formula (Ib) in the mixture is in the range from 90:10 to 99:1. It further relates to a method for producing a mixture comprising or at least essentially consisting of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib), wherein the weight ratio of the compound of the formula (Ia) to the compound of the formula (Ib) in the mixture is in the range from 90:10 to 99:1, comprising the following steps: a) providing an isomer mixture comprising or at least essentially consisting of compounds of the formula (III) (cedranediol), wherein the isomer mixture comprises or at least essentially consists of alpha,alpha-cedranediol of the formula (IIIa) and beta,beta-cedranediol of the formula (IIIb), and wherein the weight ratio of the compound of the formula (IIIa) to the compound of the formula (IIIb) in the isomer mixture is in the range from 95:5 to 99.9:0.1, b) reacting the isomer mixture from step a) with dimethoxypropane in a molar ratio of at least 1:2, based on the total molar amount of compounds of the formula (III) to the total molar amount of dimethoxypropane. It further relates to an odorant and/or aroma substance composition comprising or consisting of a mixture of the invention and also to a perfumed product comprising a mixture of the invention in a sensorially effective amount. It further relates to the use of a mixture of the invention (a) for masking or diminishing the or one or more unpleasant olfactory impression(s) of one or more unpleasantly smelling substances, and/or (b) for intensifying the or one or more pleasant olfactory impression(s) of one or more pleasantly smelling substances.

Ambrocenide® possesses the following chemical structure (formula 1):

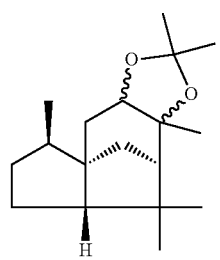

Chemical structure of Ambrocenide®

Formula 1

The squiggly lines here may denote, independently of one another, alpha- or beta-configuration. Ambrocenide® may comprise one, two, three or all of the following diastereomers (formula 2):

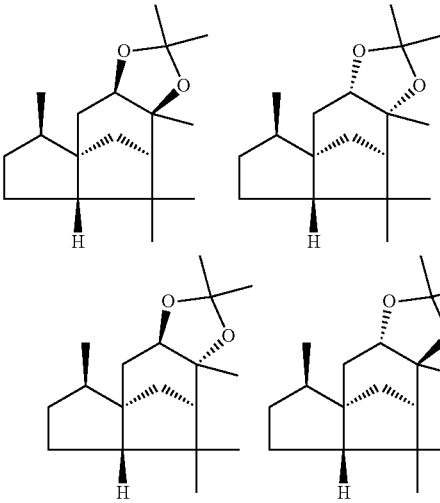

Formula 2

Diastereomers of Ambrocenide®

Accordingly, Ambrocenide® may be present in isomerically pure form as one of the stereoisomers shown in formula 2, or else as a mixture of two, three or all stated stereoisomers.

One possibility for the preparation of Ambrocenide® is first to react (−)-alpha-cedrene (1) by treatment with peracetic acid to give (−)-alpha-cedrene epoxide (2). The epoxide (2) obtained from cedrene is then converted by acid-catalyzed ring opening into a mixture of the epimeric cedrane-diols (3). Ambrocenide® (4, R=R'=CH$_3$) is obtained from the diols (3) by reaction with dimethoxypropane, with acid catalysis (formula 3).

Formula 3: Preparation of Ambrocenide® (4, R = R' = CH$_3$)

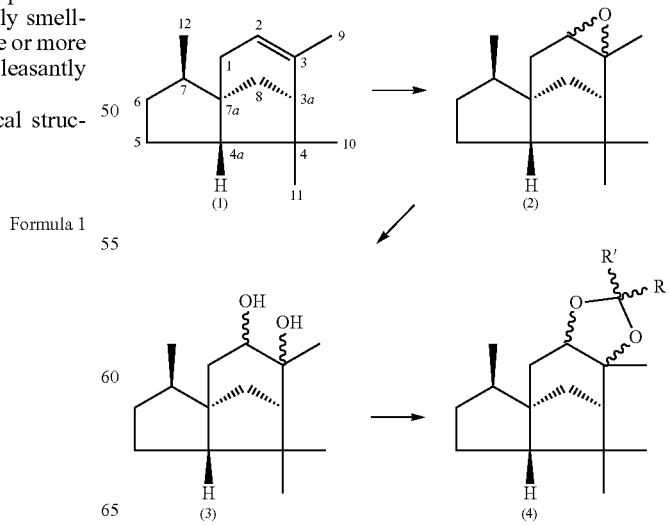

The epimerically pure epoxides (2a) and (2b) can be converted, individually or in a mixture, into the diastereomeric cedrane-diols (3a-h). Depending on the reaction conditions selected in the reaction of (−)-alpha-cedrene (1) with peracetic acid, the epimeric epoxides (2a) and (2b) may be produced in different proportions, and so, after opening of the epoxides to give the diastereomeric diols (3a-h), these too are present in different proportions (formula 4).

with dimethoxypropane, and so Ambrocenide® as well is present in the form of a diastereomer mixture.

Ambrocenide® has to date been obtainable not in crystalline form, but only as a solution, in the form for example of a 10 wt % solution in dipropylene glycol (Ambrocenide® 10DPG). It is an object of the present invention, therefore, to provide Ambrocenide® in substantially crystalline form. A "substantially crystalline form" in accordance with the

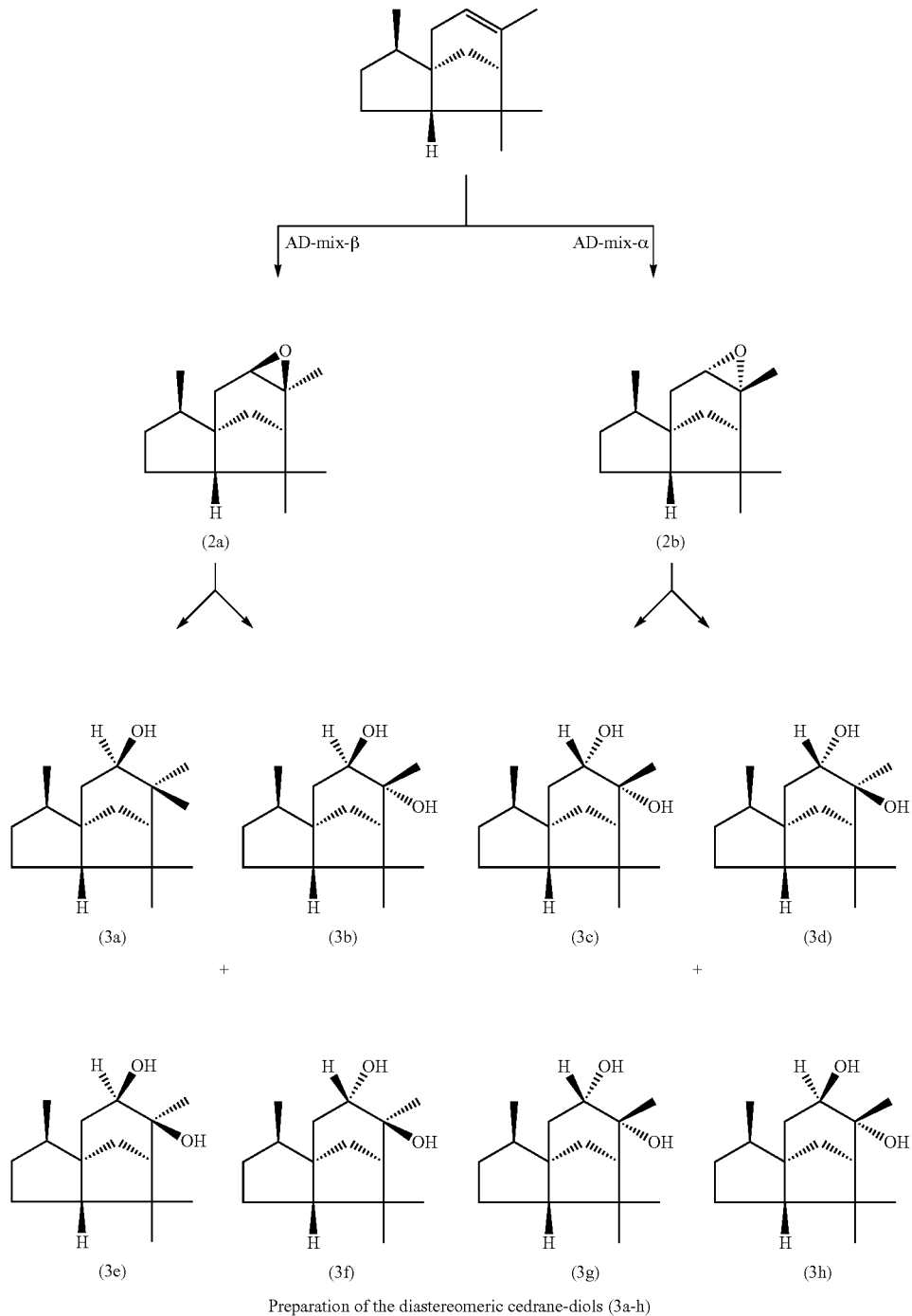

Formula 4

Preparation of the diastereomeric cedrane-diols (3a-h)

The stereochemical conditions remain substantially unchanged in the subsequent reaction of the cedrane-diols present invention means that at least 90 wt %, based on the total amount of Ambrocenide®, is in crystalline form.

This object is achieved in accordance with the invention, in a first aspect, by a mixture comprising or at least essentially consisting of compound of formula (Ia)

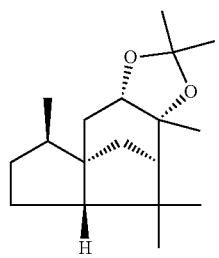

(Ia)

and (beta,beta-(4aR,5R,7aS,9R)-octahydro-2,2,5,8,8,9a-hexamethyl-4H-4a,9-methanoazuleno(5,6-d)-1,3-dioxole) of the formula (Ib),

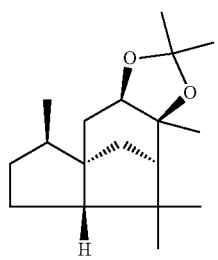

(Ib)

wherein the weight ratio of the compound of the formula (Ia) to the compound of the formula (Ib) in the mixture is in the range from 90:10 to 99:1.

By "essentially consisting of" is meant, in accordance with the present invention, that the mixture of the invention consists to an extent of at least 85 wt %, preferably at least 90 wt %, more preferably at least 95 wt %, very preferably at least 98 wt % of compounds of the formulae (Ia) and (Ib).

In one preferred embodiment the present invention relates to a mixture as herein described wherein the weight ratio of the compound of the formula (Ia) to the compound of the formula (Ib) in the mixture is in the range from 95:5 to 99:1, preferably about 98:2.

Furthermore, in another preferred embodiment, the present invention relates to a mixture as herein described wherein the mixture further comprises a compound of the formula (II) (cedralone),

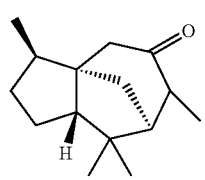

(II)

wherein the weight ratio of the total amount of compounds of the formulae (Ia) and (Ib) to the total amount of compound of the formula (II) in the mixture is at least 6:1, preferably at least 9:1, more preferably at least 12:1, very preferably at least 25:1.

The present invention likewise relates, in another preferred embodiment, to a mixture as herein described wherein the mixture further comprises a compound of the formula (III) (cedranediol),

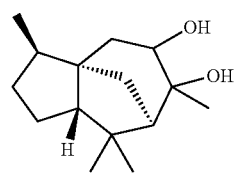

(III)

wherein the weight ratio of the total amount of compounds of the formulae (Ia) and (Ib) to the total amount of compound of the formula (III) in the mixture is at least 15:1, preferably at least 20:1, very preferably at least 25:1.

Through the present invention it is advantageously possible to provide Ambrocenide® in substantially crystalline form.

Accordingly, in one preferred embodiment, the present invention relates to a mixture of the invention as herein described wherein at least 90 wt % of the total amount of compounds of the formulae (Ia) and (Ib) in the mixture are present in crystalline form.

The mixture described herein is preferably producible by a method comprising the following steps:

a) providing an isomer mixture comprising or at least essentially consisting of compounds of the formula (III) (cedranediol), wherein the isomer mixture comprises or at least essentially consists of alpha,alpha-cedranediol of the formula (IIIa)

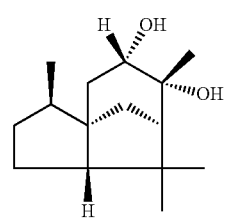

(IIIa)

and beta,beta-cedranediol of the formula (IIIb)

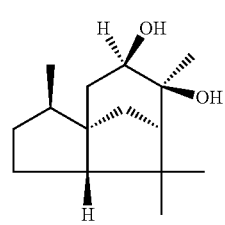

(IIIb)

and wherein the weight ratio of the compound of the formula (IIIa) to the compound of the formula (IIIb) in the isomer mixture is in the range from 95:5 to 99.9:0.1, preferably at least 98:2, b) reacting the isomer mixture from step a) with dimethoxypropane in a molar ratio of at least 1:2, based on the total molar amount of compounds of the formula (III) to the total molar amount of dimethoxypropane, and optionally c) crystallizing out the reaction product from step b) from aqueous alcoholic solution.

With regard to the above-stated step b), preference is given to reacting the isomer mixture from step a) with dimethoxypropane in a molar ratio in the range from about 1:1 to about 1:2, more particularly of about 1:2, based on the total molar amount of compounds of the formula (III) to the total molar amount of dimethoxypropane.

Accordingly, in a further aspect, the present invention also relates to a method for producing a mixture comprising or at least essentially consisting of compound of formula (Ia)

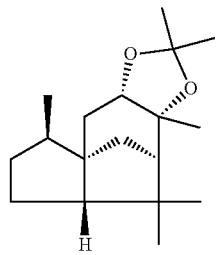

(Ia)

and beta,beta-(4aR,5R,7aS,9R)-octahydro-2,2,5,8,8,9a-hexamethyl-4H-4a,9-methanoazuleno(5,6-d)-1,3-dioxole) of the formula (Ib),

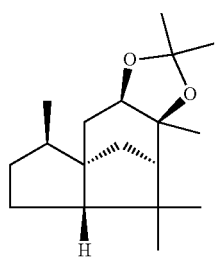

(Ib)

wherein the weight ratio of the compound of the formula (Ia) to the compound of the formula (Ib) in the mixture is in the range from 90:10 to 99:1, preferably for producing a mixture as herein described, comprising the following steps:

a) providing an isomer mixture comprising or at least essentially consisting of compounds of the formula (III) (cedranediol), wherein the isomer mixture comprises or at least essentially consists of alpha,alpha-cedranediol of the formula (IIIa)

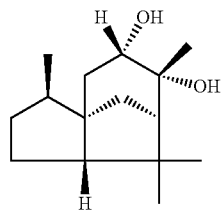

(IIIa)

and beta,beta-cedranediol of the formula (IIIb)

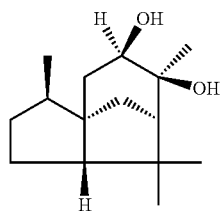

(IIIb)

and wherein the weight ratio of the compound of the formula (IIIa) to the compound of the formula (IIIb) in the isomer mixture is in the range from 95:5 to 99.9:0.1, preferably at least 98:2, b) reacting the isomer mixture from step a) with dimethoxypropane in a molar ratio of at least 1:2, based on the total molar amount of compounds of the formula (III) to the total molar amount of dimethoxypropane, optionally comprising the additional step of c) crystallizing out the reaction product from step b) from aqueous alcoholic solution.

For a method of the invention of this kind, the statements above in connection with a mixture of the invention, more particularly a preferred embodiment thereof, are valid correspondingly.

The isomer mixture comprising or at least essentially consisting of compounds of the formula (III) (cedranediol), wherein the isomer mixture comprises or at least essentially consists of alpha,alpha-cedranediol of the formula (IIIa) and beta,beta-cedranediol of the formula (IIIb), and wherein the weight ratio of the compound of the formula (IIIa) to the compound of the formula (IIIb) in the isomer mixture is in the range from 95:5 to 99.9:0.1, preferably at least 98:2, is available commercially, for example, from the company "Bio-Young Aromas Co., Ltd.", but may also be obtained, for example, by the following pathway:

A suitable amount, 100 g for example, of cedrenediol mixture (preferred cis-diol content: 85 wt %) is added with stirring to a suitable amount, 400 g for example, of a mixture of ethanol/water in a preferred weight ratio of 4:1. The reaction mixture obtained is heated preferably to 75° C. At this temperature the cedrenediol mixture dissolves completely. The reaction mixture is then stirred preferably at 75° C. for 30 minutes more and subsequently cooled to 25° C. over a period of preferably 2 hours. The precipitating crystalline solid is isolated on a suction filter and dried. Using the quantities stated above it is possible to obtain a yield of 70 g (in the form of white crystals). An exemplary analysis conducted (GC: 60° C.-240° C.; heating rate 8° C.

per minute, column type DB 1) indicated 0.8 wt % of trans-cedrenediol, 98.5 wt % of cis-cedrenediol, and 0.4 wt % of cedralone.

In a further aspect, the present invention relates to an odorant and/or aroma substance composition, preferably a perfume oil, comprising or consisting of a mixture as herein described and, furthermore, preferably one or more additional odorants and/or aroma substances.

The present invention, in one preferred embodiment, likewise relates to an odorant and/or aroma substance composition as herein described wherein the additional or one, two or more or all of the additional odorant(s) is or are selected from the group consisting of 3-(4-methyl-1-cyclohex-3-enyl)butanal, 4-(4-hydroxyphenyl)butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethylcyclohexen-1-yl)pent-1-en-3-one, (E)-4-[(1S)-1,2,6,6-tetramethylcyclohex-2-en-1-yl]but-3-en-2-one, 1-(2,6,6-trimethyl-1-cyclohex-2-enyl)pent-1-en-3-one, [(Z)-hex-3-enyl]methyl carbonate, 3-[(Z)-hex-3-enoxy]propanenitrile, 1-(2,3,8,8-tetramethyl-1,3,4,5,6,7-hexahydronaphthalen-2-yl)ethanone, spiro[1,3-dioxolane-2,5'-(4',4',8',8'-tetramethylhexahydro-3',9'-methanonaphthalene)], [3R-(3α,3aβ,6β,7β,8aα)]octahydro-6-methoxy-3,6,8,8-tetramethyl-1H-3a,7-methanoazulene, [3R-(3α,3aβ,7β,8aα)]-1-(2,3,4,7,8,8a-hexahydro-3,6,8,8-tetramethyl-1H-3a,7-methanoazulen-5-yl)ethan-1-one, 1-(2,2,6-trimethylcyclohexyl)hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl)acetate, (8E)-cyclohexadec-8-en-1-one, 16-oxacyclohexadecan-1-one, 1,3,4,6,7,8-hexahydro-4,6,6,7,8,8-hexamethylcyclopenta(g)-2-benzopyran, ethoxymethoxycyclododecane, 1,1,2,3,3-pentamethyl-2,5,6,7-tetrahydroinden-4-one, 1-(2,3,8,8-tetramethyl-1,3,4,5,6,7-hexahydronaphthalen-2-yl)ethanone.

The present invention likewise relates, in a further preferred embodiment, to an odorant and/or aroma substance composition as herein described wherein the amount of the herein-described mixture or the amount of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib) is sufficient (a) to mask or diminish the or one or more unpleasant olfactory impressions of another odorant and/or aroma substance in the odorant and/or aroma substance composition, and/or (b) to intensify the or one or more pleasant olfactory impressions of another odorant and/or aroma substance in the odorant and/or aroma substance composition.

The present invention, in another preferred embodiment, relates to an odorant and/or aroma substance composition as herein described, preferably a perfume oil, wherein the total amount of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib), based on the total weight of the odorant and/or aroma substance composition, is 0.01 to 10 wt %, preferably 0.03 to 5 wt %, more preferably 0.05 to 2 wt %.

In a further aspect, the present invention relates to a perfumed product comprising a mixture as described herein or, preferably, an odorant and/or aroma substance composition as described herein, preferably a perfume oil, in a sensorially effective amount, wherein the fraction of the mixture or of the odorant and/or aroma substance composition, based on the total weight of the product, is preferably in the range from 0.01 to 10 wt %, more preferably in the range from 0.1 to 5 wt %, very preferably in the range from 0.25 to 3 wt %.

The present invention likewise relates, in one preferred embodiment, to a perfumed product as herein described wherein the product is selected from the group consisting of perfume extracts, eau de parfums, eau de toilettes, aftershaves, eau de colognes, preshave products, splash colognes, perfumed freshening wipes, acidic, alkaline and neutral cleaners, fabric fresheners, ironing aids, liquid detergents, powder detergents, laundry pretreatment products, fabric softeners, washing soaps, washing tablets, disinfectants, surface disinfectants, air fresheners, aerosol sprays, waxes and polishes, body care products, hand creams and hand lotions, foot creams and foot lotions, hair removal creams and hair removal lotions, aftershave creams and aftershave lotions, tanning creams and tanning lotions, hair care products, deodorants and antiperspirants, decorative cosmetic products, candles, lamp oils, incense sticks, insecticides, repellants, and propellants.

In a further aspect, the present invention relates to a method for producing a perfumed product, more particularly a perfumed product as herein described, comprising the following steps:

i) providing a mixture as described above or an odorant and/or aroma substance composition as described above or the substances compound of formula (Ia)

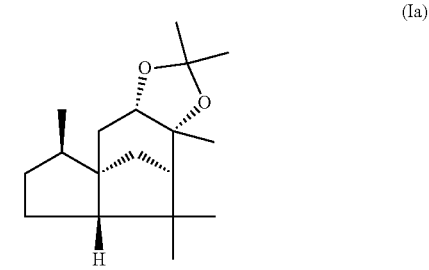 [SMILES: C[C@@H]1CC[C@H]2C(C)(C)[C@H]3C[C@@]12C[C@@H]1OC(C)(C)O[C@@]13C]

(Ia)

and (beta,beta-(4aR,5R,7aS,9R)-octahydro-2,2,5,8,8,9a-hexamethyl-4H-4a,9-methanoazuleno(5,6-d)-1,3-dioxole) of the formula (Ib),

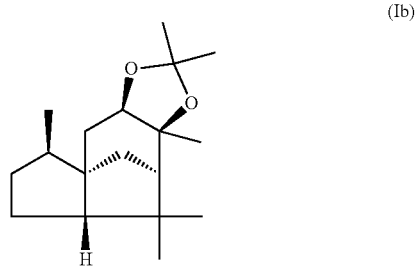 [SMILES: C[C@@H]1CC[C@H]2C(C)(C)[C@H]3C[C@@]12C[C@H]1OC(C)(C)O[C@@]31C]

(Ib)

in a weight ratio as defined in claim 1 or 2,
ii) providing one or more further constituents of the perfumed product to be produced, and
iii) contacting or mixing the further constituents provided in step ii) with a sensorially active amount of the constituents provided in step i).

In a further aspect the present invention relates to the use of a mixture as herein described
(a) for masking or diminishing the or one or more unpleasant olfactory impression or impressions of one or more unpleasantly smelling substances,
and/or
(b) for intensifying the or one or more pleasant olfactory impression(s) of one or more pleasantly smelling substances.

The present invention also relates, in one preferred embodiment, to the use as herein described in a composition, preferably a perfume oil, which comprises one or more (further) pleasantly and/or unpleasantly smelling substance(s) whose unpleasant olfactory impression is masked or diminished by the mixture as herein described and/or whose pleasant olfactory impression is intensified by the mixture as herein described, wherein this pleasantly and/or unpleasantly smelling substance or one, two or more or all of these pleasantly and/or unpleasantly smelling substances is or are selected from the group consisting of 3-(4-methyl-1-cyclohex-3-enyl)butanal, 4-(4-hydroxyphenyl)butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethylcyclohexen-1-yl)pent-1-en-3-one, (E)-4-[(1S)-1,2,6,6-tetramethylcyclohex-2-en-1-yl]but-3-en-2-one, 1-(2,6,6-trimethyl-1-cyclohex-2-enyl)pent-1-en-3-one, [(Z)-hex-3-enyl]methyl carbonate, 3-[(Z)-hex-3-enoxy]propanenitrile, 1-(2,3,8,8-tetramethyl-1,3,4,5,6,7-hexahydronaphthalen-2-yl)ethanone, spiro[1,3-dioxolane-2,5'-(4',4',8',8'-tetramethylhexa hydro-3',9'-methanonaphthalene)], [3R-(3α,3aβ,6β,7β,8aα)]octahydro-6-methoxy-3,6,8,8-tetramethyl-1H-3a,7-methanoazulene, [3R-(3α,3aβ,7β,8aα)]-1-(2,3,4,7,8,8a-hexahydro-3,6,8,8-tetramethyl-1H-3a,7-methanoazulen-5-yl)ethan-1-one, 1-(2,2,6-trimethyl-cyclohexyl)hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl)acetate, (4-methyl-1-propan-2-yl-1-cyclohex-2-enyl)acetate, (8E)-cyclohexadec-8-en-1-one, 16-oxacyclohexadecan-1-one, 1,3,4,6,7,8-hexahydro-4,6,6,7,8,8-hexamethylcyclopenta(g)-2-benzopyran, ethoxymethoxycyclododecane, 1,1,2,3,3-pentamethyl-2,5,6,7-tetrahydroinden-4-one, 1-(2,3,8,8-tetramethyl-1,3,4,5,6,7-hexahydronaphthalen-2-yl)ethanone.

The present invention likewise relates, in one preferred embodiment, to the use as herein described for intensifying the or one or more olfactory impression(s) selected from the group consisting of the odor notes floral, amber, woody, musk, violet, citrus, and aldehydic.

In a further aspect the present invention relates to a method
(a) for masking or diminishing the or one or more unpleasant olfactory impression or impressions of one or more unpleasantly smelling substances,
and/or
(b) for intensifying the or one or more pleasant olfactory impression(s) of one or more pleasantly smelling substances,
comprising the following step:
mixing the (a) pleasantly and/or (b) unpleasantly smelling substance(s) with a mixture as herein described or with an odorant and/or aroma substance composition as herein described or with the substances compound of formula (Ia)

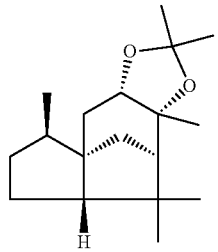

and (beta,beta-(4aR,5R,7aS,9R)-octahydro-2,2,5,8,8,9a-hexamethyl-4H-4a,9-methanoazuleno(5,6-d)-1,3-dioxole) of the formula (Ib),

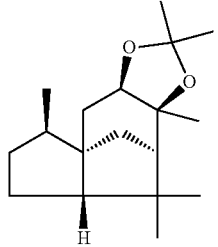

in a weight ratio as defined herein,
wherein the amount of mixture as herein described or of compound of the formula (Ia) and compound of the formula (Ib) is sufficient (a) to intensify the pleasant olfactory impression(s) of the pleasantly smelling substance(s) and/or (b) to diminish or to mask the unpleasant olfactory impression(s) of the unpleasantly smelling substance(s).

For the above-described aspects in accordance with the invention, the statements made above in connection with a mixture of the invention, more particularly a preferred embodiment thereof, are preferably valid correspondingly.

The present invention is elucidated in more detail with the following examples. Unless otherwise indicated, all amounts given are by weight.

EXAMPLE 1

Preparation of a Mixture Essentially Consisting of Compound of Formula (Ia and (beta,beta-(4aR,5R,7aS,9R)-octahydro-2,2,5,8,8,9a-hexamethyl-4H-4a,9-methanoazuleno(5,6-d)-1,3-dioxole) of the Formula (Ib)

A stirring vessel is charged with 60 kg of dimethoxypropane (95% form) in 62 kg of acetone, and this initial charge is admixed with 50 kg of an isomer mixture essentially consisting of compounds of the formula (III) (cedranediol), wherein the isomer mixture consists essentially of alpha, alpha-cedranediol of the formula (IIIa) and beta,beta-cedranediol of the formula (IIIb) and wherein the weight ratio of the compound of the formula (IIIa) to the compound of the formula (IIIb) in the isomer mixture is in the range from 95:5 to 99.9:0.1. Subsequently, over a period of 2 hours, a solution consisting of 53 kg of acetone and 0.167 kg of technical sulfuric acid is added at a temperature of not more than 30° C. After a further stirring time of 4 hours, the reaction mixture is adjusted to a pH of at least 8 with a slurry consisting of 1.6 kg of calcined sodium carbonate in 5 kg of water.

On subsequent distillation, the low boilers are removed from the reaction mixture to an extent such that a liquid-phase temperature of 95° C. is not exceeded. After the end of distillation, the distillation residue is admixed with 38 kg of methyl tert-butyl ether and stirred at a temperature of about 35° C. for around 30 minutes. The reaction mixture is then rested until a clear two-phase mixture is formed. The aqueous phase is removed and the organic phase which remains is admixed with 12 kg of water. The resulting mixture is stirred at a temperature of about 35° C. for around 30 minutes. The reaction mixture is then rested until a clear two-phase mixture is formed. The aqueous phase is removed, and on subsequent distillation of the organic phase, methyl tert-butyl ether is removed to an extent such that a liquid-phase temperature of 95° C. at 40 mbar is not exceeded. The distillation residue is taken up in 100 kg of heptane and the product is recrystallized from an aqueous ethanolic solution.

The resulting reaction product is a mixture of a total of 95 wt % consisting of compound of formula (Ia) and (beta,beta-(4aR,5R,7aS,9R)-octahydro-2,2,5,8,8,9a-hexamethyl-4H-4a,9-methanoazuleno(5,6-d)-1,3-dioxole) of the formula (Ib), where the weight ratio of the compound of the formula (Ia) to the compound of the formula (Ib) in the mixture is 95:5, and 98 wt % of the total amount of compounds of the formulae (Ia) and (Ib) in the mixture are in crystalline form.

The fraction of crystalline substance was determined by gas chromatography.

EXAMPLE 2

Perfume Oils

Reaction Product from Example 1 in the Aldehydic Sphere, Using the Following Accord as an Example:

| Ingredients | FA | FB | FC | FD | FE | FF |
|---|---|---|---|---|---|---|
| Aldehyde C11 MOA 10% 2-Methyldecanal | 285.00 | 285.00 | 285.00 | 285.00 | 285.00 | 285.00 |
| Aldehyde C11 10% Undecanal | 95.00 | 95.00 | 95.00 | 95.00 | 95.00 | 95.00 |
| Aldehyde C12 MNA 10% 2-Methylundecanal | 38.00 | 38.00 | 38.00 | 38.00 | 38.00 | 38.00 |
| Farenal ® 10% 2,6,10-Trimethyl-undec-9-enal | 76.00 | 76.00 | 76.00 | 76.00 | 76.00 | 76.00 |
| Florazone 10% 3-(4-Ethylphenyl)-2,2-dimethylpropanal | 209.00 | 209.00 | 209.00 | 209.00 | 209.00 | 209.00 |
| Limonenal 10% 3-(4-Methyl-1-cyclohex-3-enyl)butanal | 95.00 | 95.00 | 95.00 | 95.00 | 95.00 | 95.00 |
| Mandarin aldehyde 10% TEC (E)-Dodec-2-enal | 114.00 | 114.00 | 114.00 | 114.00 | 114.00 | 114.00 |
| Ozonil 10% Tridec-2-enenitrile | 38.00 | 38.00 | 38.00 | 38.00 | 38.00 | 38.00 |
| Reaction product from example 1 | — | 0.50 | 1.00 | 5.00 | 10.00 | 30.00 |
| DPG | 50.00 | 49.50 | 49.00 | 45.00 | 40.00 | 20.00 |
| Total | 1000.00 | 1000.00 | 1000.00 | 1000.00 | 1000.00 | 1000.00 |

At low levels, such as for FB and FC, a significantly stronger and more radiant development of the fragrance is observed. In FC and FD, moreover, the typical aldehydic, fatty, and metallic character of the accord is emphasized, this being very surprising on account of the difference in fragrance profile. From FE onward, the influence of the reaction product from example 1 is predominant, giving the accord a highly ambery odor. Specifically in comparison to Ambrocenide® 10DPG, the reaction product from example 1 is integrated more effectively into the accord and underlines its strengths, such as cleanness and freshness, whereas Ambrocenide® 10DPG also imparts strength, but has woody elements which give it a not so clear and clean effect.

Reaction Product from example 1 in the Citrus Sphere, Using the Following Accord as an Example:

| Ingredients | AA | AB | AC | AE | AF | AG |
|---|---|---|---|---|---|---|
| Amarocit ® 6,6-Dimethoxy-2,5,5-trimethylhex-2-ene | 60.00 | 60.00 | 60.00 | 60.00 | 60.00 | 60.00 |
| Lemon Oil Ital. | 210.00 | 210.00 | 210.00 | 210.00 | 210.00 | 210.00 |
| Orange Terpenes | 80.00 | 80.00 | 80.00 | 80.00 | 80.00 | 80.00 |
| Claritone ® 2,4,4,7-Tetramethyl-oct-6-en-3-one | 80.00 | 80.00 | 80.00 | 80.00 | 80.00 | 80.00 |
| Dihydromyrcenol 2,6-Dimethyloct-7-en-2-ol | 150.00 | 150.00 | 150.00 | 150.00 | 150.00 | 150.00 |
| Linalool 3,7-Dimethylocta-1,6-dien-3-ol | 150.00 | 150.00 | 150.00 | 150.00 | 150.00 | 150.00 |
| Linalyl acetate 3,7-Dimethylocta-1,6-dien-3-yl acetate | 50.00 | 50.00 | 50.00 | 50.00 | 50.00 | 50.00 |
| Terpinyl acetate (4-Methyl-1-propan-2-yl-1-cyclohex-2-enyl) acetate | 50.00 | 50.00 | 50.00 | 50.00 | 50.00 | 50.00 |
| Vertacetal ® Coeur 2,4,6-Trimethyl-4-phenyl-1,3-dioxane | 20.00 | 20.00 | 20.00 | 20.00 | 20.00 | 20.00 |
| Reaction product from example 1 | — | 10.00 | 30.00 | 50.00 | 100.00 | 150.00 |
| DPG | 150.00 | 140.00 | 120.00 | 100.00 | 150.00 | — |
| Total | 1000.00 | 1000.00 | 1000.00 | 1000.00 | 1100.00 | 1000.00 |

The reaction product from example 1 enters the note easily in spite of its ambery fragrance, and underlines the natural citrus character of the accord with typical citrus, lactone undertones. Added at higher levels, it develops into a more perfumistic accord, in which the reaction product from example 1 represents the base note. Specifically in comparison to Ambrocenide® 10DPG, it integrates more effectively into the fragrance, and has a clearer, more radiant and, in particular, more natural effect.

Reaction Product from Example 1 in the Violet Sphere, Using the Following Accord as an Example:

| Ingredients | AA | AD | AF | AG | AH | AI |
|---|---|---|---|---|---|---|
| Cetone Alpha (E)-3-Methyl-4-(2,6,6-trimethyl-1-cyclohex-2-enyl)but-3-en-2-one | 10.00 | 10.00 | 10.00 | 10.00 | 10.00 | 10.00 |
| Evernyl 10% Methyl 2,4-dihydroxy-3,6-dimethylbenzoate | 20.00 | 20.00 | 20.00 | 20.00 | 20.00 | 20.00 |
| Frambinon ® 1% 4-(4-Hydroxy-phenyl)butan-2-one | 40.00 | 40.00 | 40.00 | 40.00 | 40.00 | 40.00 |
| Helional 3-(1,3-Benzodioxol-5-yl)-2-methylpropanal | 5.00 | 5.00 | 5.00 | 5.00 | 5.00 | 5.00 |
| Hedione Methyl 3-oxo-2-pentyl-cyclopentaneacetate | 60.00 | 60.00 | 60.00 | 60.00 | 60.00 | 60.00 |
| Heliotropin 1,3-Benzodioxole-5-carbaldehyde | 10.00 | 10.00 | 10.00 | 10.00 | 10.00 | 10.00 |
| Ionone Alpha (E)-4-(2,6,6-Trimethyl-1-cyclohex-2-enyl)but-3-ene-2-one | 80.00 | 80.00 | 80.00 | 80.00 | 80.00 | 80.00 |
| Ionone Beta 4-(2,6,6-Trimethyl-cyclohexen-1-yl)but-3-en-2-one | 40.00 | 40.00 | 40.00 | 40.00 | 40.00 | 40.00 |
| Iraldein Beta (E)-1-(2,6,6-Trimethyl-cyclohexen-1-yl)pent-1-en-3-one | 110.00 | 110.00 | 110.00 | 110.00 | 110.00 | 110.00 |
| Iron Alpha 10% (E)-4-[(1S)-1,2,6,6-Tetramethylcyclohex-2-en-1-yl]but-3-en-2-one | 20.00 | 20.00 | 20.00 | 20.00 | 20.00 | 20.00 |

-continued

| Ingredients | AA | AD | AF | AG | AH | AI |
|---|---|---|---|---|---|---|
| Isoraldein 70 1-(2,6,6-Trimethyl-1-cyclohex-2-enyl)pent-1-en-3-one | 425.00 | 425.00 | 425.00 | 425.00 | 425.00 | 425.00 |
| Leafovert ® 10% [(Z)-Hex-3-enyl] methyl carbonate | 15.00 | 15.00 | 15.00 | 15.00 | 15.00 | 15.00 |
| Nonadienal 0.1% (2E,6Z)-Nona-2,6-dienal + (2E,4E)-nona-2,4-dienal | 10.00 | 10.00 | 10.00 | 10.00 | 10.00 | 10.00 |
| Parmanyl ® 3-[(Z)-Hex-3-enoxy]propanenitrile | 20.00 | 20.00 | 20.00 | 20.00 | 20.00 | 20.00 |
| *Patchouli* oil | 5.00 | 5.00 | 5.00 | 5.00 | 5.00 | 5.00 |
| Syvertal 10% 2-Heptan-3-yl-1,3-dioxolane | 10.00 | 10.00 | 10.00 | 10.00 | 10.00 | 10.00 |
| Violet Leaves Abs. 1% | 20.00 | 20.00 | 20.00 | 20.00 | 20.00 | 20.00 |
| Reaction product from example 1 | — | 5.00 | 10.00 | 20.00 | 50.00 | 100.00 |
| DPG | 100.00 | 95.00 | 90.00 | 80.00 | 50.00 | — |
| Total | 1000.00 | 1000.00 | 1000.00 | 1000.00 | 1000.00 | 1000.00 |

Added especially at low levels such as in AD, an iris root aspect is significantly emphasized by the reaction product from example 1. In AF it underlines the ionone elements of the accord. In AG, the ambery character is markedly noticeable, but not unpleasant.

Reaction Product from Example 1 in the Musk Sphere, Using the Following Accord as an Example:

| Ingredients | AA | AB | AC | AD | AE | AF |
|---|---|---|---|---|---|---|
| Aurelione (7E)-Cyclohexadec-7-en-1-one | 100.00 | 100.00 | 100.00 | 100.00 | 100.00 | 100.00 |
| Globalide (3E)-Oxacyclohexadec-3-en-2-one | 300.00 | 300.00 | 300.00 | 300.00 | 300.00 | 300.00 |
| Globanone (8E)-Cyclohexadec-8-en-1-one | 200.00 | 200.00 | 200.00 | 200.00 | 200.00 | 200.00 |
| Macrolide Supra 16-Oxacyclohexadecan-1-one | 200.00 | 200.00 | 200.00 | 200.00 | 200.00 | 200.00 |
| Galaxolide 1,3,4,6,7,8-Hexahydro-4,6,6,7,8,8-hexamethyl-cyclopenta(g)-2-benzopyran | 100.00 | 100.00 | 100.00 | 100.00 | 100.00 | 100.00 |
| Reaction product from example 1 | — | 1.00 | 5.00 | 90.00 | 50.00 | 100.00 |
| DPG | 100.00 | 99.00 | 95.00 | 10.00 | 50.00 | — |
| Total | 1000.00 | 1000.00 | 1000.00 | 1000.00 | 1000.00 | 1000.00 |

The reaction product from example 1 provides surprisingly good assistance to the soft musk character of the accord. It gives the musk, which is known as a base note, with better perceptibility and strength even in the initial odor. Added at higher levels, from AD onward, the amber note becomes clearly perceptible, but even up to AF it is not perceived as negative, instead forming an attractive harmonic complex. In comparison to this, Ambrocenide® 10DPG is found to be much flatter and less radiant.

Reaction Product from Example 1 in the Woody Sphere, Using the Following Accord as an Example:

| Ingredients | AA | AB | AC | AD | AE |
|---|---|---|---|---|---|
| Iso E Super 1-(2,3,8,8-Tetramethyl-1,3,4,5,6,7-hexahydronaphthalen-2-yl)ethanone | 320.00 | 320.00 | 320.00 | 320.00 | 320.00 |
| Ysamber® K Spiro[1,3-dioxolane-2,5'-(4',4',8',8'-tetramethylhexahydro-3',9'-methanonaphthalene)] | 230.00 | 230.00 | 230.00 | 230.00 | 230.00 |
| Cedramber [3R-(3α,3aβ,7β,8aα)]-Octahydro-6-methoxy-3,6,8,8-tetramethyl-1H-3a,7-methanoazulene | 30.00 | 30.00 | 30.00 | 30.00 | 30.00 |
| Vertofix [3R-(3α,3aβ,7β,8aα)]-1-(2,3,4,7,8,8a-Hexahydro-3,6,8,8-tetramethyl-1H-3a,7-methanoazulen-5-yl)ethan-1-one | 70.00 | 70.00 | 70.00 | 70.00 | 70.00 |
| Timberol® 1-(2,2,6-Trimethyl-cyclohexyl)hexan-3-ol | 200.00 | 200.00 | 200.00 | 200.00 | 200.00 |
| Reaction product from example 1 | — | 20.00 | 50.00 | 100.00 | 150.00 |
| DPG | 150.00 | 130.00 | 100.00 | 150.00 | — |
| Total | 1000.00 | 1000.00 | 1000.00 | 1100.00 | 1000.00 |

In AB, the reaction product from example 1 supports the woody character of the accord and gives it radiance and strength. In AC it makes the accord more dryly woody and gives it an ambery undertone. Added at the higher levels, a wood-amber accord is formed.

Reaction Product from Example 1 in the Amber Sphere, Using the Following Accord as an Example:

| Ingredients | CA | CB | CC | CD | CE | CF |
|---|---|---|---|---|---|---|
| Amberwood® F Ethoxymethoxycyclododecane | 200.00 | 200.00 | 200.00 | 200.00 | 200.00 | 200.00 |
| Cashmeran 1,1,2,3,3-Pentamethyl-2,5,6,7-tetrahydroinden-4-one | 40.00 | 40.00 | 40.00 | 40.00 | 40.00 | 40.00 |
| Iso E Super 1-(2,3,8,8-Tetramethyl-1,3,4,5,6,7-hexahydronaphthalen-2-yl)ethanone | 250.00 | 250.00 | 250.00 | 250.00 | 250.00 | 250.00 |
| Madranol 3-Methyl-4-(2,2,6-trimethylcyclohexyl)butan-2-ol | 200.00 | 200.00 | 200.00 | 200.00 | 200.00 | 200.00 |
| Ambrinol S 10% 2,5,5-Trimethyl-1,3,4,4a,6,7-hexahydronaphthalen-2-ol | 20.00 | 20.00 | 20.00 | 20.00 | 20.00 | 20.00 |
| Ambroxide Cryst. (3aR,5aS,9aS,9bR)-3a,6,6,9a-Tetramethyl-2,4,5,5a,7,8,9,9b-octahydro-1H-benzo[e][1]benzofuran | 110.00 | 110.00 | 110.00 | 110.00 | 110.00 | 110.00 |
| Ysamber® K Spiro[1,3-dioxolane-2,5'-(4',4',8',8'-tetramethyl-hexahydro-3',9'-methanonaphthalene)] | 100.00 | 100.00 | 100.00 | 100.00 | 100.00 | 100.00 |
| Ambrarome 10% Base composed of various constituents | 25.00 | 25.00 | 25.00 | 25.00 | 25.00 | 25.00 |
| Lactoscatone Hexahydro-3,5,5-trimethyl-3,8a-ethano-8ah-1-benzopyran-2(3H)-one | 5.00 | 5.00 | 5.00 | 5.00 | 5.00 | 5.00 |
| Reaction product from example 1 | — | 1.00 | 5.00 | 10.00 | 20.00 | 50.00 |
| DPG | 50.00 | 49.00 | 45.00 | 40.00 | 30.00 | — |
| Total | 1000.00 | 1000.00 | 1000.00 | 1000.00 | 1000.00 | 1000.00 |

From the lowest to the highest level of addition, the reaction product from example 1 supports the amber note, gives it complexity, and makes the note more radiant, more ambery, and more lively. In comparison to this, Ambrocenide® 10DPG also strengthens the accord, but otherwise tends to remain in the background; it provides volume, but in the higher added levels tends to turn off into a somewhat dirty, animal direction.

EXAMPLE 3

Perfumed Products

Detergent Powder:

| Ingredient | Weight fractions |
|---|---|
| Aldehyde C11 Undecylic 10% | 16.00 |
| Aldehyde C11 Undecylenic 10% | 18.00 |
| Aldehyde C12 Laurie 10% | 14.00 |
| Aldehyde C12 MNA 10% | 12.00 |
| Hexenal trans-2 10% | 4.00 |
| Hexenyl acetate cis-3 | 4.00 |
| Vertocitral | 10.00 |
| Magnolan | 130.00 |
| Mintonat | 35.00 |
| Dihydro Myrcenol | 70.00 |
| Orange Oil | 35.00 |
| Nerolione 10% | 3.50 |
| Cantryl ® | 3.50 |
| Hexyl Acetate | 18.00 |
| Jasmaprunat | 18.00 |
| Aldehyde C14 So-Called | 50.00 |
| Ethyl methyl butyrate-2 | 8.00 |
| Manzanate | 1.20 |
| Allyl Cyclohexyl Propionate | 8.00 |
| Aprifloren ® | 3.00 |
| Fruitate | 1.80 |
| Ethyl linalool | 56.00 |
| Dimethyl Benzyl Carbinyl Butyrate | 7.00 |
| Rose Abs. Type Base | 30.00 |
| Rosaphen ® | 30.00 |
| Damascenone Total | 1.20 |
| Damascone Alpha | 1.80 |
| Benzyl Acetate | 28.00 |
| Hedione | 56.00 |
| Hexyl Cinnamic Aldehyde Alpha | 130.00 |
| Parmanyl ® | 3.50 |
| Isoraldeine 70 | 28.00 |
| Isoeugenyl Acetate | 3.50 |
| Agrumex HC | 50.00 |
| Ambroxide Cryst. | 1.50 |
| Reaction product from example 1 | 0.80 |
| Dipropylene glycol | 109.70 |
| Total | 1000.00 |

The reaction product from example 1 here underlines the warm woody base note and assists attachment to the laundry.

Shampoo:

| Ingredient | Weight fractions |
|---|---|
| Hexenol cis-3 | 2.50 |
| Galbanum Oil 10% | 5.00 |
| Magnolan | 25.00 |
| Bergamot Oil RCO | 80.00 |
| Linalyl Acetate | 120.00 |
| Lemon Oil | 80.00 |
| Neroli Base | 10.00 |
| Lavender Oil | 6.00 |
| Thyme Oil 10% | 6.00 |

-continued

| Ingredient | Weight fractions |
|---|---|
| Linalool | 60.00 |
| Phenylethyl Alcohol BA Free | 20.00 |
| Vitessence ® Rose De Mai | 6.50 |
| Narcisse Abs. 10% | 1.30 |
| Hedione | 80.00 |
| Jasmolactone Cis 10% | 6.00 |
| Parmanyl ® 10% | 12.70 |
| Ionone Beta | 6.00 |
| Methyl Ionone Gamma Pure | 18.00 |
| Irone Alpha 10% | 12.00 |
| Benzoin Siam Resin 50% | 5.00 |
| Coumarin | 5.00 |
| iso E Super | 180.00 |
| Cashmeran | 12.00 |
| Isobutyl Quinoline 10% | 6.00 |
| Reaction product from example 1 | 0.2 |
| Globalide ® | 45.00 |
| Dipropylene glycol | 189.80 |
| Total | 1000.00 |

The reaction product from example 1 here strengthens not only the head note but also the attaching woody elements in the base note.

The invention claimed is:

1. An odorant and/or aroma mixture comprising at least 85 wt. %, based on the total weight of the mixture, of a compound of formula (Ia) and a compound of formula (Ib)

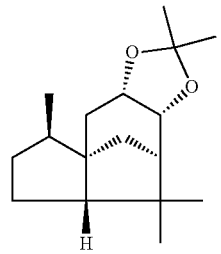

formula (Ia)

(alpha,alpha-(4aR,5R,7aS,9R)-octahydro-2,2,5,8,8,9a-hexamethyl-4H-4a,9-methanoazuleno(5,6-d)-1,3-dioxole)

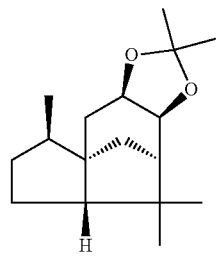

formula (Ib)

(beta,beta-(4aR,5R,7aS,9R)-octahydro-2,2,5,8,8,9a-hexamethyl-4H-4a, 9-methanoazuleno(5,6-d)-1,3-dioxole), wherein, the weight ratio of the total amount of the compound of formula (Ia) to the total amount of the compound of formula (Ib) is from 90:10 to 99:1, and at least 90 wt. % of the total amount of the compound of formula (Ia) and the compound of formula (Ib) is in crystalline form.

2. The odorant and/or aroma mixture as claimed in claim 1, wherein the weight ratio of the total amount of the compound of formula (Ia) to the total amount of the compound of formula (Ib) is from 95:5 to 99:1 and the mixture further comprises a compound of formula (II),

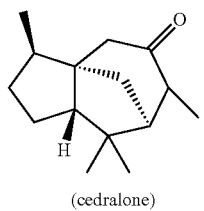

(cedralone)

wherein the weight ratio of the total amount of the compound of formula (Ia) and the compound of formula (Ib) to the total amount of the compound of formula (II) is at least 6:1.

3. The odorant and/or aroma mixture as claimed in claim 2, wherein the weight ratio of the total amount of the compound of formula (Ia) and the compound of formula (Ib) to the total amount of the compound of formula (II) is at least 25:1.

4. The odorant and/or aroma mixture as claimed in claim 1, wherein the weight ratio of the total amount of the compound of formula (Ia) to the total amount of the compound of formula (Ib) is from 95:5 to 99:1.

5. The odorant and/or aroma mixture as claimed in claim 1, wherein the mixture further comprises a compound of formula (II),

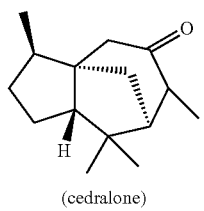

(cedralone)

wherein the weight ratio of the total amount of the compound of formula (Ia) and the compound of formula (Ib) to the total amount of the compound of formula (II) is at least 12:1.

6. The odorant and/or aroma mixture as claimed in claim 1, wherein the mixture further comprises a compound of formula (III),

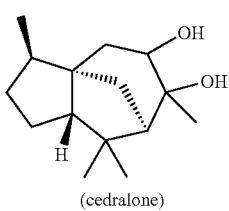

(cedralone)

wherein the weight ratio of the total amount of the compound of formula (Ia) and the compound of formula (Ib) to the total amount of the compound of formula (III) is at least 15:1.

7. A odorant and/or aroma mixture as claimed in claim 1, producible by a method comprising:
a) providing an isomer mixture comprising a compound of formula (IIIa) and a compound of formula (IIIb)

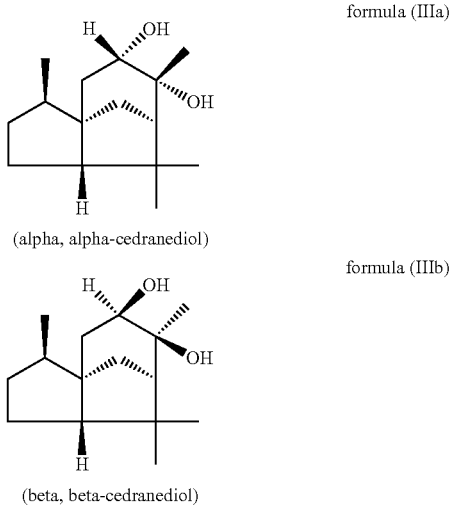

(alpha, alpha-cedranediol)

(beta, beta-cedranediol)

wherein the weight ratio of the total amount of the compound of formula (IIIa) to the total amount of the compound of formula (IIIb) is from 95:5 to 99.9:0.1,
b) reacting the isomer mixture from a) with dimethoxypropane in a molar ratio of at least 1:2, based on the total molar amount of the compound of formula (IIIa) and the compound of formula (IIIb) to the total molar amount of dimethoxypropane, and
c) crystallizing out the reaction product from step b) from an aqueous alcoholic solution.

8. An odorant and/or aroma substance composition comprising an odorant and/or aroma mixture as claimed in claim 1 and one or more additional odorants and/or aroma substances.

9. The odorant and/or aroma substance composition as claimed in claim 8, wherein the total amount of the compound of formula (Ia) and the compound of formula (Ib) is:
(a) sufficient to mask or diminish one or more unpleasant olfactory impressions of another odorant and/or aroma substance in the odorant and/or aroma substance composition, and/or
(b) sufficient to intensify one or more pleasant olfactory impressions of another odorant and/or aroma substance in the odorant and/or aroma substance composition.

10. The odorant and/or aroma substance composition as claimed in claim 8, wherein the total amount of the compound of formula (Ia) and the compound of formula (Ib) is from 0.01 to 10 wt %, based on the total weight of the odorant and/or aroma substance composition.

11. A perfumed product comprising an odorant and/or aroma mixture as claimed in claim 1 in an amount from 0.01 to 10 wt %, based on the total weight of the product, wherein the product is selected from perfume extracts, eau de parfums, eau de toilettes, aftershaves, eau de colognes, preshave products, splash colognes, perfumed freshening wipes, acidic, alkaline and neutral cleaners, fabric fresheners, ironing aids, liquid detergents, powder detergents, laundry pretreatment products, fabric softeners, washing soaps, washing tablets, disinfectants, surface disinfectants, air fresheners, aerosol sprays, waxes and polishes, body care products, hand creams and hand lotions, foot creams and foot lotions, hair removal creams and hair removal lotions, aftershave creams and aftershave lotions, tanning creams and tanning lotions, hair care products, deodorants and antiperspirants, decorative cosmetic products, candles, lamp oils, incense sticks, insecticides, repellants, and propellants.

12. A method for producing a perfumed product comprising:
i) providing a mixture as claimed in claim 1,
ii) providing one or more further constituents of the perfumed product to be produced, and
iii) contacting or mixing the further constituents provided in ii) with a sensorially active amount of the mixture of i).

13. A method for:
(a) masking or diminishing one or more unpleasant olfactory impression or impressions of one or more unpleasantly smelling substances, and/or
(b) intensifying one or more pleasant olfactory impression(s) of one or more pleasantly smelling substances, comprising:
mixing the unpleasantly smelling substances of (a) and/or the pleasantly smelling substances of (b) with a mixture as claimed in claim 1.

14. The method of claim 13 for intensifying the or one or more pleasant olfactory impression(s) of one or more pleasantly smelling substances, wherein the one or more pleasantly smelling substances are selected from the group consisting of odor notes of floral, amber, woody, musk, violet, citrus, and aldehydic.

15. The method of claim 13, wherein the pleasantly and/or unpleasantly smelling substance are selected from the group consisting of 3-(4-methyl-1-cyclohex-3-enyl)butanal, 4-(4-hydroxyphenyl)butan-2-one, (E)-4-(2,6,6-trimethyl-1-cyclohex-2-enyl)but-3-en-2-one, (E)-4-(2,6,6-trimethyl-1-cyclohex-2-enyl)but-3-en-2-one, (E)-1-(2,6,6-trimethyl-cyclohexen-1-yl)pent-1-en-3-one, (E)-4-[(1S)-1,2,6,6-tetramethylcyclohex-2-en-1-yl]but-3-en-2-one, 1-(2,6,6-trimethyl-1-cyclohex-2-enyl)pent-1-en-3-one, [(Z)-hex-3-enyl] methyl carbonate, 3-[(Z)-hex-3-enoxy]propanenitrile, 1-(2,3,8,8-tetramethyl-1,3,4,5,6,7-hexahydronaphthalen-2-yl)ethanone, spiro[1,3-dioxolane-2,5'-(4', 4',8', 8'-tetramethylhexahydro-3',9'-methanonaphthalene)], [3R-(3α,3aβ,6β,7β,8aα)]octahydro-6-methoxy-3,6,8,8-tetramethyl-1H-3a,7-methanoazulene, [3R-(3α,3aβ,7β,8aα)]-1-(2,3,4,7,8,8a-hexahydro-3,6,8,8-tetramethyl-1H-3a,7-methanoazulen-5-yl)ethan-1-one, 1-(2,2,6-trimethylcyclohexyl)hexan-3-ol, 6,6-dimethoxy-2,5,5-trimethylhex-2-ene, 2,6-dimethyloct-7-en-2-ol, 3,7-dimethylocta-1,6-dien-3-ol, (3,7-dimethylocta-1,6-dien-3-yl) acetate, (4-methyl-1-propan-2-yl-1-cyclohex-2-enyl) acetate, (8E)-cyclohexadec-8-en-1-one, 16-oxacyclohexadecan-1-one, 1,3,4,6,7,8-hexahydro-4,6,6,7,8,8-hexamethylcyclopenta(g)-2-benzopyran, ethoxymethoxycyclododecane, 1,1,2,3,3-pentamethyl-2,5,6,7-tetrahydroinden-4-one, 1-(2,3,8,8-tetramethyl-1,3,4,5,6,7-hexahydronaphthalen-2-yl)ethanone.

16. The odorant and/or aroma substance mixture of claim 1, further comprising crystalline ambroxide.

17. An odorant and/or aroma mixture consisting of:
(a) at least 95 wt. %, based on the total weight of the mixture, of compounds of formula (Ia) and compounds of formula (Ib)

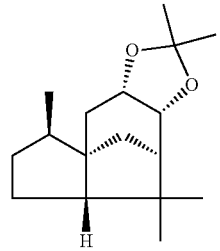

formula (Ia)

(alpha,alpha-(4aR,5R,7aS,9R)-octahydro-2,2,5,8,8,9a-hexamethyl-4H-4a,9-methanoazuleno(5,6-d)-1,3-dioxole)

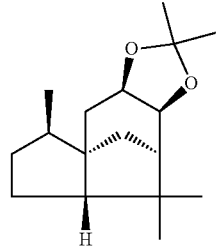

formula (Ib)

(beta,beta-(4aR,5R,7aS,9R)-octahydro-2,2,5,8,8,9a-hexamethyl-4H-4a,9-methanoazuleno(5,6-d)-1,3-dioxole);
wherein, the weight ratio of the total amount of the compound of formula (Ia) to the total amount of the compound of formula (Ib) is from 90:10 to 99:1, and
at least 90 wt % of the total amount of the compound of formula (Ia) and the compound of formula (Ib) is in crystalline form (b) optionally, a compound of formula (II)

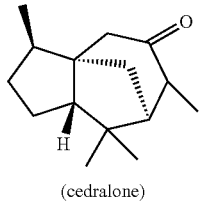

formula (II)

(cedralone)

wherein the weight ratio of the total amount of the compound of formula (Ia) and the compound of formula (Ib) to the total amount of the compound of formula (II) is at least 12:1; and (c) optionally, a compound of formula (III)
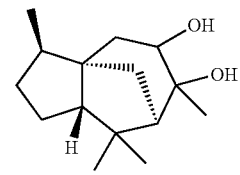
formula (III)
(cedralone)
wherein the weight ratio of the total amount of the compound of formula (Ia) and the compound of (Ib) to the total amount of the compound of formula (III) is at least 20:1.
* * * * *